United States Patent
Goto et al.

[11] Patent Number: 5,100,584
[45] Date of Patent: Mar. 31, 1992

[54] NON-LINEAR OPTICAL DEVICE

[75] Inventors: Yoshitaka Goto, Tsukuba; Zhang G. Jian, Kawasaki; Masaharu Nakayama, Tsuchiura, all of Japan

[73] Assignee: Nippon Oil and Fats Co., Ltd., Tokyo, Japan

[21] Appl. No.: 629,147

[22] Filed: Dec. 18, 1990

[30] Foreign Application Priority Data

Dec. 25, 1989 [JP] Japan .................... 1-332578

[51] Int. Cl.$^5$ .......................... F21V 9/00; F21V 9/04; G02F 1/13; G02B 6/00
[52] U.S. Cl. .................... 252/582; 252/587; 252/589; 359/328; 385/122
[58] Field of Search .......... 252/582, 587, 589, 299.61; 350/352, 3.64, 96.34, 96.3, 350 R

[56] References Cited

PUBLICATIONS

CA:107 197992g, "Organoarsonium compounds", Tao et al., p. 731, vol. 107(25), Chemical Abstract, 1987.
CA:89 215296z, "Reactions of furan analogs of chalcones with diazomethane", Dorofeeva et al., Chemical abstract vol. 89(25), 1978.
CA:95 6929t, "Synthesis of 1-(2-furyl)-3-phenyl-2-propen-1-one derivatives", Tulecki et al., Chemical Abstract vol. 95(21), 1981.
Hawley's Condensed Chemical Dictionary, 11th Ed., Van Nostrand Reinhold Co., New York, New York, 1987.

Primary Examiner—Robert L. Stoll
Assistant Examiner—Shean C. Wu
Attorney, Agent, or Firm—Darby & Darby

[57] ABSTRACT

A non-linear optical device is provided in which an organic compound is disposed in a light beam. The organic compound is a benzalacetofuran derivative represented by the following formula (I)

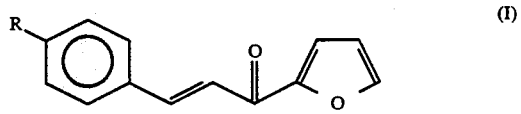

(I)

wherein R is $CH_3$, $CH_3S$, Br, CN or $NO_2$.

2 Claims, 1 Drawing Sheet

NON-LINEAR OPTICAL DEVICE

BACKGROUND OF THE INVENTION

This invention relates to a non-linear optical device which consists of a benzalacetofuran derivative.

Non-linear optical materials are the materials exhibiting so-called non-linear optical effects, in which non-linear responses result from induced polarization of electrons by the electrical field created by the light incident on the materials. These optical effects are generally due to the second and higher order terms in the following equation of $$P = \chi^1 E + \chi^2 E \cdot E + \chi^3 E \cdot E \cdot E + \cdots + \chi^n E \cdot n$$

wherein P is polarizability of a material, E is intensity of electrical field, and $\chi^n$ is non-linear optical susceptibility of the n'th order.

It has been known that, due to a phenomen known as the second harmonic generation (SHG) obtained by the specific utilization of the secondary effect, an incident light is converted into a light wave corresponding to the second harmonic wave and having a frequency twice as high as the frequency of the incident light or the refractive index is changed by voltage, so that the phenomenon is very conveniently utilized for performing various optical processings including conversion of wavelengths, processing of signals and modulation of laser beams, which are extremely advantageous.

Although inorganic crystals, such as $KH_2PO_4$ (KDP), $LiNbO_3$ or $NH_4H_2PO_4$ (ADP), have hitherto been used as the non-linear optical materials, they have disadvantages that single crystals having high optical purities are very expensive, that they are so deliquescent as to be inconvenient in handling, and that the non-linear sensitivities thereof are not so high. On the other hand, since the utility of organic materials was suggested in 1983 in the symposium in the American Chemical Society, organic crystals of urea, aniline base compounds or the like have been reported to be utilizable as non-linear optical materials. However, these organic compounds do not exhibit satisfactory non-linear optical effects, or the compounds which exhibit relatively high level of non-linear effect have a disadvantage that they have light absorptive terminal groups that are significantly shifted towards the long wavelength range to thus limit the wavelength range of the light waves which can be processed therethrough.

SUMMARY OF THE INVENTION

It is an object of the present invention to provide a non-linear optical device consisting of a benzalacetofuran derivative with the specific structure, having excellent transparency and superior transmission and exhibiting extremely high non-linear optical effects.

According to the present invention, there is provided non-linear optical device in which an organic compound is disposed in a light beam, the organic compound being a benzalacetofuran derivative represented by the following formula (I)

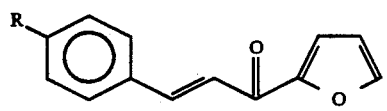

(I)

wherein R is $CH_3$, $CH_3S$, Br, CN or $NO_2$.

PREFERRED EMBODIMENTS OF THE INVENTION

Figure 1:
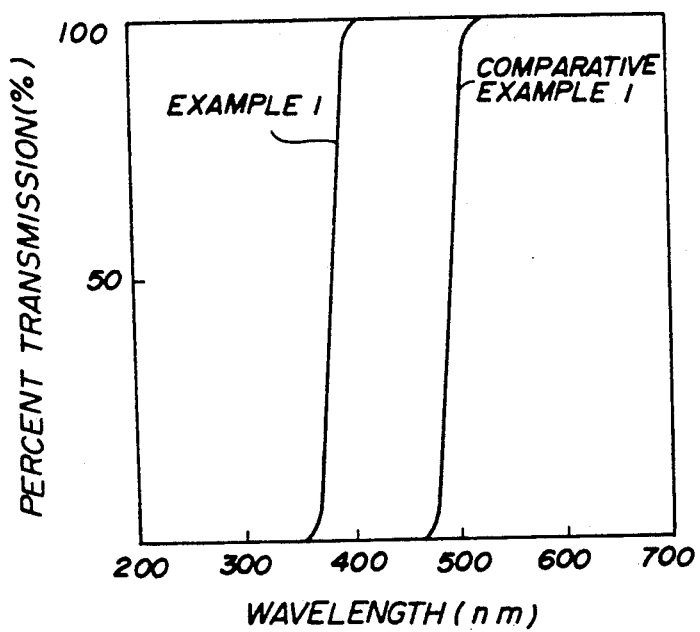
FIG. 1 is a chart showing the light absorption spectrum of a known non-linear optical material and the light absorption spectrum of a purified product of 4-methyl benzalacetofuran which is employed in the non-linear optical device of the present invention.

The present invention will be explained in detail hereinbelow.

In a non-linear optical device of the present invention, an organic compound is disposed in a light beam.

A benzalacetofuran derivative, employed as the organic compound of the present invention, is represented by the following formula (I):

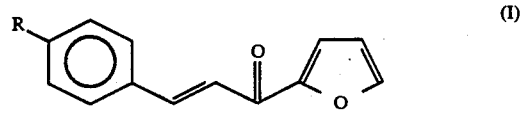

(I)

wherein R is $CH_3$, $CH_3S$, Br, CN or $NO_2$.

The benzalacetofuran derivative represented by the formula (I) is selected from the group consisting of 4-methyl benzalacetofuran, 4-methylthio benzalacetofuran, 4-bromo benzalacetofuran, 4-cyano benzalacetofuran, 4-nitro benzalacetofuran and mixtures thereof.

In preparing the benzalacetofuran derivative represented by the formula (I), 2-acetofuran and each of 4-methyl benzaldehyde, 4-methylthio benzaldehyde, 4-bromo benzaldehyde, 4-cyano benzaldehyde or 4-nitro benzaldehyde may be subjected to dehydration condensation reaction in the presence of a basic catalyst or an acidic catalyst. Sodium hydroxide, potassium hydroxide or a variety of quaternary ammonium salts may be employed as the basic catalysts, while boron trifluoride, phosphorous oxychloride or boron trifluoride etherate may be employed as the acidic catalysts. More specifically, the benzalacetofuran derivative of the present invention may be obtained by reacting 2-acetofuran and the specific benzaldehyde in the temperature range of preferably 0° to 50° C. for 30 minutes to 50 hours in the presence of the above mentioned catalysts, if necessary, in suitable solvents, e.g. alcohols such as methanol or ethanol. The reaction temperature higher than 50° C. is not desirable since various secondary reactions are produced by heat, whereas the reaction temperature lower than 0° C. is also not desirable since the reaction time is prolonged with concomitant economical disadvantages.

The above specific benzalacetofuran derivative may be employed directly or may be purified by recrystallization.

In the non-linear optical device of the present invention, the benzalacetofuran derivative is employed so that it exhibits extremely high non-linear optical effects as well as excellent transparency and superior transmission for the wavelength having not less than 400 nm and hence may be used for a variety of optical applications.

EXAMPLES OF THE INVENTION

The present invention will be explained in more detail with reference to Examples and Comparative Examples.

EXAMPLE 1

1.1 g (0.01 mol) of 2-acetofuran and 1.16 g (0.01 mol) of 4-methyl benzaldehyde were charged, along with 20 ml of ethanol, into a reaction vessel, and stirred at 25° C. while a mixed solution of 1 g of a 40 wt % aqueous solution of sodium hydroxide and 10 ml of ethanol was added dropwise to the reaction system. After termination of adding the mixed solution dropwise, the reaction was practiced at 25° C. for 24 hours. After 20 ml of a 0.5 N aqueous solution of hydrochloric acid was added to the reaction system to terminate the reaction, a precipitated solid was filtered, washed several times with distilled water and dried.

The so-produced crude product was recrystallized with an ethanol solvent to obtain 1.91 g of purified 4-methyl benzalacetofuran melting at 111.0° C. at a yield of 90%.

Anal. calcd. for $C_{14}H_{12}O_2$: C 79.23% ; H 5.70%.
Found : C 79.41% ; H 5.64%.

The light transmission spectrum is shown in FIG. 1.

EXAMPLES 2 to 5

The procedures similar to Example 1 were followed except that benzaldehyde as a starting material was changed to 4-methylthio benzaldehyde (example 2), 4-bromo benzaldehyde (example 3), 4-cyano benzaldehyde (example 4) or 4-nitro benzaldehyde (example 5). The following products of the Examples 2 to 5 were similarly synthesized in accordance with the Example 1. Each of the products was analyzed in accordance with the example 1. The following are the results.

Products Obtained in Example 2

4-methylthio benzalacetofuran melting point : 122.7° C.

Anal.calcd. for $C_{14}H_{12}SO_2$: C 68.83% ; H 4.95% ; S 13.12%.
Found : C 67.95 ; S 13.22%.

Product obtained in Example 3

4-bromo benzalacetofuran melting point : 131.3° C.

Anal.calcd. for $C_{13}H_9BrO_2$: C 56.35% ; H 3.27% ; Br 28.83%
Found : C 56.07% ; H 3.19% ; Br 28.97%.

Product obtained in Example 4

4-cyano benzalacetofuran melting point : 187.9° C.

Anal.calcd. for $C_{14}H_9NO_2$:
C 75.35% ; H 4.04% ; N 6.28%.
Found : C 75.85% ; H 4.17% ; N 6.09%.

Product Obtained in Example 5

4-nitro benzalacetofuran melting point : 228.4° C.

Anal. calcd. for $C_{14}H_9NO_4$: C 65.90% ; H 3.53% ; N 5.49%.

Found C 65.72% ; H 3.61% ; N 5.75%.

EXAMPLE 6

The measurement of the second harmonic generation (SHG) of the produced compounds in the Examples 1 to 5 were then performed. For measurement, each of the samples was granulated to the size of 50 to 150 um in diameter and sandwiched between a pair of slide glasses. Each sample was irradiated with 15 nsec pulses by an $Nd^+$-YAG laser fitted with a Q-switch (wavelength : 1064 nm) to detect the second harmonics emanated from the sample. An urea sample, granulated in the similar manner, was used as a standard sample, and the ratio of the SHG strength or intensity of the sample was found with respect to the SHG strength of the urea which was set to 1. This method of measurement is well-known among those engaged in the art and described in detail in, for example, Journal of Applied Physics, vol. 36, No. 8, pages 3798 to 3813, 1968.

The SHG intensity ratio of respective benzalacetofuran derivatives of the present invention is shown in Table 1.

Comparative Example 1

The light transmission spectrum of 2-methyl-4-nitro aniline, which is a well-known non-linear optical material, was measured and the result of the light transmission spectrum is shown in FIG. 1.

Comparative Examples 2 to 4

4-ethyl benzalacetofuran (Comparative Example 2), 4-chloro benzalacetofuron (Comparative Example 3) and 4-iodo benzalacetofuran (Comparative Example 4) were similarly synthesized in accordance with Example 1. The SHG intensity ratio of the products in the Comparative Examples 2 to 4 were measured in accordance with the Example 6. The results of the SHG intensity ratio are shown in Table 1. The produced respective compounds in the Comparative Examples 2 to 4 did not exhibit non-linear optical activity.

TABLE 1

| | Structure Formula | SHG Intensity Ratio |
|---|---|---|
| Example 1 | $CH_3$— | 15.3 |
| Example 2 | $CH_3S$— | 41.5 |
| Example 3 | Br— | 13.7 |

TABLE 1-continued

| | Structure Formula | SHG Intensity Ratio |
|---|---|---|
| Example 4 | 4-CN-C6H4-CH=CH-C(O)-furan | 17.2 |
| Example 5 | 4-NO2-C6H4-CH=CH-C(O)-furan | 11.5 |
| Comparative Example 1 | NH2-C(=O)-NH2 (urea) | 1.0 |
| Comparative Example 2 | 4-CH3CH2-C6H4-CH=CH-C(O)-furan | 0 |
| Comparative Example 3 | 4-Cl-C6H4-CH=CH-C(O)-furan | 0 |
| Comparative Example 4 | 4-I-C6H4-CH=CH-C(O)-furan | 0 |

Obviously from FIG. 1, the product of the Example 1 of the present invention exhibited transmission of about 100% for the wavelength having not less than 400 nm and was substantially transparent. On the contrary, with respect to 2-methyl-4-nitro aniline, which is the known non-linear optical material, the visible ray having the wavelength of 500 nm or smaller was absorbed and was not transmitted.

Although the present invention has been described with reference to the specific examples, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. In a non-linear optical device in which an organic compound is disposed in a light beam, the improvement in which the organic compound is a benzalacetofuran derivative represented by the following formula (I)

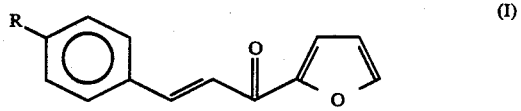

wherein R is $CH_3$, $CH_3S$, Br, CN or $NO_2$.

2. The non-linear optical device according to claim 1 wherein said benzalacetofuran derivative is selected from the group consisting of 4-methyl benzalacetofuran, 4-methylthio benzalacetofuran, 4-bromo benzalacetofuran, 4-cyano benzalacetofuran, 4-nitro benzalacetofuran and mixtures thereof.

* * * * *